United States Patent [19]

Berges

[11] 4,079,134

[45] Mar. 14, 1978

[54] 7-ACYLAMINO-3-(5-SULFOMETHYL-1,3,4-THIADIAZOL-2-YLTHIOMETHYL)-3-CEPHEM-4-CARBOXYLIC ACIDS

[75] Inventor: David A. Berges, Wayne, Pa.

[73] Assignee: SmithKline Corporation, Philadelphia, Pa.

[21] Appl. No.: 726,378

[22] Filed: Sep. 24, 1976

[51] Int. Cl.$^2$ ............... C07D 501/36; A61K 31/545
[52] U.S. Cl. ..................... 424/246; 544/26; 544/27
[58] Field of Search ............ 260/243 C; 424/246; 544/29, 26, 27

[56] References Cited

FOREIGN PATENT DOCUMENTS

| 818,209 | 11/1974 | Belgium | 260/243 C |
| 823,861 | 6/1975 | Belgium. | |
| 2,446,901 | 4/1975 | Germany. | |

*Primary Examiner*—Nicholas S. Rizzo
*Attorney, Agent, or Firm*—William H. Edgerton

[57] ABSTRACT

New semisynthetic cephalosporins characterized by having structures with a 5-sulfomethyl-1,3,4-thiadiazol-2-ylthiomethyl group at position 3. Exemplary is the anti-bacterially effective 7-D-mandelamido-3-(5-sulfomethyl-1,3,4-thiadiazol-2-ylthiomethyl)-3-cephem-4-carboxylic acid disodium salt.

6 Claims, No Drawings

7-ACYLAMINO-3-(5-SULFOMETHYL-1,3,4-THIADIAZOL-2-YLTHIOMETHYL)-3-CEPHEM-4-CARBOXYLIC ACIDS

This invention relates to a new series of cephalosporin compounds having antibacterial activity and to intermediates useful for preparing them. The structures of the new compounds are characterized by having at the 3-position a sulfoalkyl-substituted 1,3,4-thiadiazole group.

Exemplary of the compounds of this invention are those represented by the following structural formula:

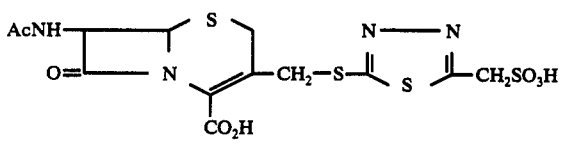

in which Ac represents a pharmaceutically acceptable acyl group known to be of utility as a substituent on the 7-amino group in the structures of known or prior art cephalosporins or on the 6-amino group in the structures of known or prior art penicillins with the proviso that Ac does not contain a substituted or unsubstituted thiazole (or thiazoline) moiety.

Representative acyl substituents are:

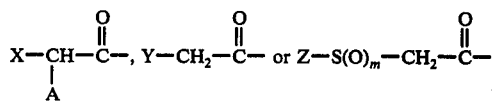

wherein:

X is thienyl, furyl, phenyl or phenyl monosubstituted with hydroxy, hydroxymethyl, formamido or ureido;

A is $NH_2$, OH, COOH, $SO_3H$, formyloxy or, when the α-C-hydrogen is absent, methoxyimino;

Y is cyano, sydnone, pyridone, thienyl, o-aminomethylphenyl, phenoxy, phenyl or tetrazolyl;

Z is methyl, trifluoromethyl, trifluoroethyl, pyridyl or cyanomethyl; and m is zero to two.

Each of the three partial structures above represent subgeneric groups of compounds covered by this invention.

Representative 7-acylamino substituents of the compounds of Formula I are listed below;
α-hydroxyphenylacetamido
α-aminophenylacetamido
α-amino-4-hydroxyphenylacetamido
trifluoromethylthioacetamido
2,2,2-trifluoroethylsulfinylacetamido
2,2,2-trifluoroethylthioacetamido
cyanoacetamido
α-carboxythienylacetamido
α-carboxyphenylacetamido
α-sulfophenylacetamido
methylsulfonylacetamido
cyanomethylthioacetamido
3-sydnoneacetamido
1-tetrazolylacetamido
2-thienylacetamido
syn-2-methoxyimino-2-α-furylacetamido
4-pyridylthioacetamido
o-aminomethylphenylacetamido Others together with N-acylation procedures may be found in Cephalosporins and Penicillins, Flynn, Academic Press, 1972; U.S. Pat. Nos. 2,721,196 and 3,953,424; Belgian Pat. No. 832,725; German Pat. Nos. 2,127,285 and 2,406,165.

It will be recognized that the 4-carboxylic acid group of the compounds of Formula I may be readily esterified by methods well known to the art. These esters include, for example, simple alkyl and aryl esters as well as esters which are easily cleaved, within the body, to the parent acid such as indanyl, pivaloyloxymethyl, acetoxymethyl, propionyloxymethyl, glycyloxymethyl, phenylglycyloxymethyl and thienylglycyloxymethyl esters and others. Of course, when A is COOH, this group may be similarly esterified. All such ester derivatives are included within the scope of this invention.

Also covered in this invention are the pharmaceutically acceptable, nontoxic derivatives of the compounds of Formula I from which they derive utility: the salts, as stated above easily split ester or ether derivatives of either a carboxy or hydroxy function, amide derivatives at an amino radical such as in a 7-glycylamino group as the furyl-, pyranyl-, oxolanyl- or oxiranyl- carbonyl amides (i.e. Belgian Pat. No. 835,295), the solvates such as hydrates, glycolates or alcoholates. As examples of these one skilled in the art would be able to prepare and use the alkali metal salts such as the sodium or potassium salts (for example using sodium or potassium 2-ethyl hexanoate), ammonium salts, organic amine salts such as those with procaine or dibenzylethylenediamine.

Other known cephalosporin modifications can be made by known synthetic procedures such as introduction of an α-methoxy group at position 7, preferably at the stage of the 7-aminocephalosporanic acid reactants disclosed below (IV), prior to N-acylation. Optical isomers are also possible such as with the mandeloyl or phenylglycyl substituents at 7. The D-forms of these subgeneric groups are preferred.

The compounds of this invention are most conveniently prepared by a displacement of the acetoxy group of a known 7-acylaminocephalosporanic acid (II) by 5-sulfomethyl-1,3,4-thiadiazole-2-thiol (III). Alternatively a similar displacement with the thiol can be run on 7-aminocephalosporanic acid to give 7-amino-3-(5-sulfomethyl-1,3,4-thiadiazol-2-ylthiomethyl)-3-cephem-4-carboxylic acid (IV) which may then be N-acylated as known to the art as described above. Suitable protective groups may be used in either method as is known to the art (see "Protective Groups in Organic Chemistry", J. F. W. McOmie, Plenum Press, 1973, Chapters 2 and 3 for use of amino, carboxy, sulfo or hydroxyl protective groups). For example the t-butyl (for COOH) or t-butoxycarbonyl (for $NH_2$) groups are easily removed by treatment with trifluoroacetic acid.

The compounds of Formula I have antibacterial activity against either Gram positive or Gram negative bacteria with minimum inhibitory concentrations (MIC's) in vitro from 0.4 to 200 μg/ml. Test results for 7-D-mandelamido-3-(5-sulfomethyl-1,3,4-thiadiazol-2-ylthiomethyl)-3-cephem-4-carboxylic acid, disodium salt, tetrahydrate (A) are:

|  | A | Cefazolin | Cephalothin |
| --- | --- | --- | --- |
| S. aureus HH 127 | 1.6 | 0.4 | 0.4 |
| S. aureus SK 23390 | 0.4 | 0.2 | 0.1 |

-continued

| | A | Cefazolin | Cephalothin |
|---|---|---|---|
| S. aureus villaluz SK 70390 | 200 | 100 | 50 |
| Strep. Faecalis HH 34358 | 25 | 6.3 | 6.3 |
| E. coli SK 12140 | 0.4 | 0.8 | 3.1 |
| E. coli HH 33779 | 0.8 | 1.6 | 6.3 |
| Kleb. pneumo. SK 4200 | 0.4 | 1.6 | 1.6 |
| Kleb. pneumo. SK 1200 | 0.4 | 0.8 | 1.6 |
| Salmonella ATCC 12176 | 0.4 | 0.8 | 1.6 |
| Pseudo. aeru. HH 63 | >200 | >200 | >200 |
| Serratia marc. ATCC 13880 | 25 | >200 | >200 |
| Proteus morgani 179 | 1.6 | >200 | >200 |
| Entero. aerog. ATCC 13048 | 1.6 | 1.6 | 12.5 |
| Entero. cloacae HH 31254 | 0.4 | 0.8 | 6.3 |
| Proteus mirabilis PN-444 | 0.4 | 3.1 | 0.8 |

Compound A gave an $ED_{50}$ in mice of 0.3 and 0.39 mg/kg against E. coli as well as 0.78 and 0.62 mg/kg against Kleb. pneumo. (s.c.); 25 and 10 mg/kg against E. coli as well as 8.7 and 8.5 mg/kg against Kleb. pneumo. (p.o.). Cephalexin gives comparable values of 12.5 (11.3); 16.5 (16.5); 21.5 (18); 19 (10) respectively.

The data show that the sulfoalkylthiadiazole-containing cephalosporins are more potent than the sulfoalkyloxadiazole-containing cephalosporins of my copending application, Ser. No. 666,095 filed Mar. 11, 1976 especially against the Gram negative organisms and especially by the oral route as demonstrated by the in vivo tests in infected mice.

Pharmaceutical compositions having antibacterial activity which comprise a pharmaceutical carrier containing an active but nontoxic quantity of a compound of Formula I as well as methods of combatting bacterial infections by administering such a composition to an infected animal or human host in a nontoxic amount sufficient to combat such infections are also objects of this invention. The administration may be orally or by parenteral injection such as subcutaneously, intramuscularly or intravenously. The injection of suitably prepared sterile solutions or suspensions containing an effective, nontoxic amount of the new cephalosporin compound is the preferred route of administration.

The compounds of Formula I are formulated and administered in the same manner as other prior art cephalosporins such as cephazolin or cephalothin. The dosage regimen comprises administration, preferably by injection, of an active but nontoxic quantity of a compound of Formula I selected from the dosage unit range of from about 100 mg to 500 mg with the total daily dosage regimen being from about 500 mg to 6 g. The compounds as their sodium or potassium salts are very water soluble compared with non-sulfo containing congeners in the art. The precise dosages are dependent upon the age and weight of the subject and on the susceptibility of the infection being treated to each individual compound. These can be determined by those skilled in the art based on the data disclosed herein compared with that available to the art attained with the known cephalosporins outlined herebefore.

The following examples illustrate the invention but are not to be construed as limiting the scope thereof. Temperatures are in degrees Centigrade (° C.) unless otherwise stated.

EXAMPLE 1

A solution of 15.6 g (0.1 mol) of p-methoxybenzyl chloride in 25 ml of ethanol was added dropwise to a solution of 14.6 g (0.1 mol) of potassium dithiocarbazate in 200 ml of 1:1 aqueous ethanol. After stirring for 2 hours at room temperature, the mixture was cooled in an ice bath to precipitate 16.4 g of the desired product, p-methoxybenzyl dithiocarbazate, m.p. 138.5°–140° after recrystallization from chloroform.

Anal. Calculated: C, 47.34; H, 5.30; N, 12.27; Found: C, 47.55; H, 5.32; N, 12.59.

A solution of 6.15 g (0.055 mol) of chloroacetyl chloride in 50 ml of dry benzene was added dropwise to a suspension of 11.4 g of the dithiocarbazate in 250 ml of benzene. The mixture was stirred at room temperature then heated at reflux for 4 hours over a water trap. The cooled reaction mixture was washed with water, dilute sodium bicarbonate then water. The dried organic layers were evaporated to leave a yellow oil which crystallized upon standing. The solid was purified by extraction with hot hexane (6 × 150 ml). The soluble material obtained after evaporation of the hexane extracts was crystallized using methylene chloride-hexane to give 9.15 g of the desired 2-(p-methoxybenzylthio)-5-chloromethyl-1,3,4-thiadiazole, m.p. 60.5°–63.5°.

Anal. Calculated: C, 46.07; H, 3.87; N, 9.77 Found: C, 46.33; H, 4.04; N, 9.78.

A mixture of 13.0 g of the chloromethylthiadiazole in 250 ml of tetrahydrofuran and 5.73 g of sodium sulfite in 50 ml of water was heated at reflux overnight. Since reaction was not complete, a solution of 2.86 g of sodium sulfite in 100 ml of water was added again followed by refluxing overnight. The mixture was then evaporated. The residue was extracted into 275 ml of warm water which was extracted with ethyl ether. The aqueous phase was evaporated to about 200 ml volume. Cooling gave 8.6 g of white platelets of the desired 5-(p-methoxybenzylthio)-1,3,4-thiadiazole-2-methanesulfonic acid, sodium salt.

A solution of 31.2 g (0.091 mol) of mercuric acetate in 240 ml of water was added to a solution of 11.6 g of thio compound prepared immediately above in 480 ml of methanol and 125 ml of water. After 1.5 hours the mixture was treated with hydrogen sulfide until it was completely black. The mixture was evaporated, methanol was added and the black solid was removed by filtration. Evaporation of the methanol solution gave a crystalline solid which was purified by recrystallization from water-propanol.

A second crop can be isolated from the filtrate to give a total of 5.18 g (68%), m.p. 293° of 5-mercapto-1,3,4-thiadiazole-2-methanesulfonic acid or 5-sulfomethyl-1,3,4-thiadiazole-2-thiol as the sodium salt. The parent acid may be obtained by passing an aqueous solution of the sodium salt down a column of strongly acidic ion-exchange resin and then evaporating the water. Other alkali metal salts may be prepared from the acid such as the potassium salt using potassium methoxide-methanol. These are new intermediate compounds and are part of this invention.

A solution of 6.4 g (0.015 mol) of 7-D-mandelamidocephalosporanic acid sodium salt, 2.3 g (0.01 mol) of the thiol salt in 75 ml of water was treated with sodium bicarbonate to pH 6.7. The mixture was warmed at 68° for 5 hours. The cooled mixture was taken to pH 2.0 with 6N sulfuric acid after addition of ethyl acetate. The mixture was extracted twice with ethyl acetate. The remaining aqueous phase was passed over an XAD-7 column (a crosslinked polymer of acrylic esters with an average pore diameter of 80A) with elution with water. The product containing eluates were combined and evaporated. The solid was put on a column of cellulose powder in 80:20 acetonitrile:water. The product containing eluates were evaporated to the water content then passed over IR-120-HCP resin. The acidified solution was titrated from pH 2.0 to pH 6.5 with 2% sodium hydroxide solution. The solution was filtered and lyophilized to give 7-[D-(-)-mandelamido]-3-(5-sulfomethyl-1,3,4-thiadiazol-2-ylthiomethyl)-3-cephem-4-carboxylic acid, disodium salt tetrahydrate.

Anal. Calculated: C, 33.82; H, 3.59; N, 8.30 Found: C, 34.08; H, 3.44; N, 8.14.

EXAMPLE 2

A mixture of 5.22 g (10.0 mmol) of 7-(D-α-t-butoxycarbonylamino-4-hydroxyphenylacetamido)cephalosporanic acid and an excess (15.0 mmol) of 5-sulfomethyl-1,3,4-thiadiazole-2-thiol in 75 ml of pH 6.4 phosphate buffer solution is treated with sufficient sodium bicarbonate to give a pH of 6.4. The mixture is heated at 70° for 3 hours, cooled, acidified with dilute hydrochloric acid to pH 2 and extracted with ethyl acetate. The aqueous solution is adjusted to pH 7.0 with sodium bicarbonate and added to an XAD-7 column. Elution with water and then methanol followed by evaporation of the product-containing fractions gives the t-boc derivative of the desired compound as its disodium salt. This derivative is stirred at 25° C. with 25 ml of trifluoroacetic acid and 25 ml of 1,3-dimethoxybenzene for 2 hours. The mixture is evaporated to dryness, ether added to the residue and the precipitated salt collected. This is dissolved in water, and one molecular equivalent of sodium bicarbonate is added. The solution is lyophilized and then triturated with acetone to give 7-(D-α-amino-4-hydroxyphenylacetamido)-3-(5-sulfomethyl-1,3,4-thiadiazol-2-ylthiomethyl)-3-cephem-4-carboxylic acid. Similar treatment of the t-boc derivative of the 7-DL-(α-aminophenylacetamidocephalosporanic acid gives the corresponding 7-DL-(α-aminophenylacetamido)-3-(5-sulfomethyl-1,3,4-thiadiazol-2-ylthiomethyl)-3-cephem-4-carboxylic acid.

EXAMPLE 3

A mixture of an excess (12.2 mmol) of 5-sulfomethyl-1,3,4-thiadiazole-2-thiol, 32.5 mol of sodium bicarbonate and 8.1 mmol of 7-trifluoromethylthioacetamidocephalosporanic acid in 50 ml of water is stirred at 70° for 5 hours. The reaction mixture is cooled and passed over XAD-2 resin with water and methanol as eluants. The methanol eluants are evaporated to dryness to give a residue which is dissolved in a small amount of water and lyophilized to give 7-trifluoromethylthioacetamido-3-(5-sulfomethyl-1,3,4-thiadiazol-2-ylthiomethyl)-3-cephem-4-carboxylic acid disodium salt. Substituting 7-(2-thienylacetamido)-cephalosporanic acid gives 7-(2-thienylacetamido)-3-(5-sulfomethyl-1,3,4-thiadiazol-2-ylthiomethyl)-3-cephem-4-carboxylic acid disodium salt.

Stoichiometric quantities of cephalosporanic acids having the individual 7-acylamino substituent listed hereabove may be substituted in Examples 1–3 with variations which will be obvious to those skilled in this art.

EXAMPLE 4

An injectable pharmaceutical composition is formed by adding sterile saline solution (2 ml) to 350 mg of the product of Example 1. This material is injected parenterally four times daily to a human patient infected with susceptible bacteria. Other compounds of this invention may be similarly used.

What is claimed is:

1. A compound of the structural formula:

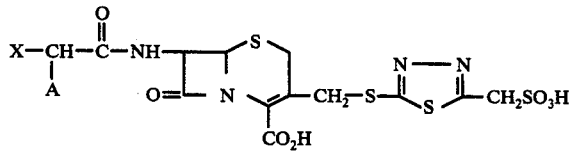

in which:
X is thienyl, furyl, phenyl or phenyl monosubstituted with hydroxy, hydroxymethyl, formamido or ureido; and
A is $NH_2$, OH, COOH, $SO_3H$, formyloxy or when the α-C-hydrogen is absent, methoxyimino;
or its nontoxic pharmaceutically acceptable alkali metal salts.

2. The compound of claim 1 being 7-D-mandelamido-3-(5-sulfomethyl-1,3,4-thiadiazol-2-ylthiomethyl)-3-cephem-4-carboxylic acid.

3. The compound of claim 1 being 7-D-mandelamido-3-(5-sulfomethyl-1,3,4-thiadiazol-2-ylthiomethyl)-3-cephem-4-carboxylic acid disodium salt.

4. The compound of claim 1 being 7-(D-α-amino-4-hydroxyphenylacetamido)-3-(5-sulfomethyl-1,3,4-thiadiazol-2-ylthiomethyl)-3-cephem-4-carboxylic acid.

5. A pharmaceutical composition having antibacterial activity comprising a compound as claimed in claim 1 and a pharmaceutically acceptable carrier therefor.

6. A method of treating bacterial infections comprising administering internally to an infected or susceptible human subject an antibacterially effective but nontoxic dose of a compound as claimed in claim 1.

* * * * *